United States Patent [19]

Livshits et al.

[11] Patent Number: 5,534,421
[45] Date of Patent: Jul. 9, 1996

[54] **PRODUCTION OF ISOLEUCINE BY *ESCHERICHIA COLI* HAVING ISOLEUCINE AUXOTROPHY AND NO NEGATIVE FEEDBACK INHIBITION OF ISOLEUCINE PRODUCTION**

[75] Inventors: Vitaly A. Livshits; Vladimir G. Debabov; Aaveilova O. Fedorovva; Zakataeva N. Pavlovva; Rustem S. Shakulov; Tatyana A. Bachina; Evgeny M. Khurges, all of Moscow, Russian Federation

[73] Assignee: Ajinomoto Co., Inc., Tokyo, Japan

[21] Appl. No.: 116,601

[22] Filed: Sep. 7, 1993

Related U.S. Application Data

[62] Division of Ser. No. 707,616, May 30, 1991.

[51] Int. Cl.$^6$ .............................. C12P 13/06; C12P 13/08
[52] U.S. Cl. ...................... 435/116; 435/115; 435/172.1; 435/183; 435/252.8
[58] Field of Search ..................................... 435/116, 183, 435/252.8, 172.1, 115

[56] References Cited

U.S. PATENT DOCUMENTS 4,278,765  7/1981  Debabov et al. ..................... 435/172.3
4,388,405  7/1983  Sano et al. ......................... 435/252.33

FOREIGN PATENT DOCUMENTS 872984  5/1987  WIPO.

OTHER PUBLICATIONS

Iaccarino et al., "Isoleucine Auxotrophy as a Consequence of a Mutationally Altered Isoleucyl–transfer Ribonucleic Acid Synthetase," *J Bacteriology*, vol. 185 No. 2, pp. 527–537, 1971.

Mizukami et al., "Essential Role of Aspartokinase in L–Threonine Production by *Escherichia coli* W Mutants," *Agric Biol. Chem.* vol. 50, No. 4, pp. 1015–1018, 1986.

Roth et al., "Histidine Regulatory Mutants in *Salmonella typhimurium*", *J. Mol. Biol.*, vol. 22, pp. 325–334, 1966.

R. P. Lawther, et al, Proc. Natl. Acad. Sci. USA, vol. 78, pp. 922–925 (1981).

R. P. Lawther, et al, J. of Bacteriology, vol. 149, pp. 294–298 (1982).

*Primary Examiner*—Herbert J. Lilling
*Attorney, Agent, or Firm*—Oblon, Spivak, McClelland, Maier & Neustadt

[57] ABSTRACT

The present invention provides strains of *Escherichia coli* which have an isoleucine-tRNA synthetase with an increased Km and no negative feedback inhibition of isoleucine production. These strains are effective for the production of isoleucine in high amounts.

9 Claims, No Drawings

PRODUCTION OF ISOLEUCINE BY ESCHERICHIA COLI HAVING ISOLEUCINE AUXOTROPHY AND NO NEGATIVE FEEDBACK INHIBITION OF ISOLEUCINE PRODUCTION

This is a division of application Ser. No. 07/707,616, filed on May 30, 1991.

FIELD OF THE INVENTION

The present invention relates to the microbiological industry and, more specifically, it relates to a method for preparing strains which produce amino acids.

DISCUSSION OF THE BACKGROUND

Amino acids produced by microorganisms find extensive use as feedstuff and food additives in the agriculture and food industry, as components of various nutrient mixtures for medical purposes and as reagents in the chemical and pharmaceutical industries.

Known in the art are methods for preparing strains which produce amino acids such as L-lysine, L-threonine, L-isoleucine, L-valine and the like by using various mutagens. The resulting mutant strains of microorganisms have specific genetically preconditioned defects in regulating metabolism and, due to such defects, they evolve into the nutrient medium, or produce specific amino acids. The required strains of microorganisms are produced by conventional methods based on the particular nutritive demand of a mutant (auxotrophy) or on resistance of a mutant to one or another structural analogue of an amino acid inhibiting the growth of the parental strain.

Amino acid production by known auxotrophic strains results from blocking the formation of a by-product or a coinhibitor amino acid, which participate in the negative control of the amino acid biosynthesis. Known are pantothenate auxotrophs of *Escherichia coli*, producing valine (Maas, W. K., Vogel, H. J., *J. Bacteriol.*, v. 65, p. 388, 1953), homoserine-requiring strains of *Corynebacterium glutamicum* and *Brevibacterium flavum*, producing lysine (Nakayama et al., *J. Gen. Appl. Microbiol.*, v. 7, p. 41, 1961), isoleucine-, threonine-, or homoserine-requiring mutants of *Arthrobacter paraffineus* and *Corynebacterium hydrocarboclastus* producing valine (U.S. Pat. No. 3,700,556).

Amino acid production by mutant strains resistant to structural analogues of amino acids results from destroying the negative regulation of the amino acid biosynthesis, i.e., feed-back inhibition of the key enzyme activity or repression of the corresponding enzyme's formation by the end products. Known are the S-2-aminoethyl-L-cysteine resistant mutant of genus Brevibacterium producing lysine (Sano, K., Shiio, I., *J. Gen. Appl. Microbiol.*, v. 16, p. 373, 1970, Shiio et al., *J. Biochem.*, v. 68, p. 701, 1970), the amino-hydroxy-valeric acid (AHV) resistant mutant of *Escherichia coli* producing threonine (Shiio, I., Nakamoris, *Agr. Biol. Chem.*, v. 33, p. 1152, 1969), AHV resistant mutant of the Brevibacterium producing threonine and the mutant of microorganisms belonging to the genus Brevibacterium or Corynebacterium, resistant to aminohydroxyvaleric acid producing isoleucine (U.S. Pat. No. 3,767,529), mutant strains of the genera Brevibacterium and Corynebacterium having resistance to 2-thiasolalanine which produce valine (U.S. Pat. No. 3,893,888), mutant strains of *Serratia marcescens* resistant to isoleucine hydroxamate producing isoleucine (Kisumi et al, *J. Bacteriol.*, v. 110, p. 761, 1972).

Amino acid-producing strains having a resistance to an amino acid analogue together with a nutrient requirement which increases their productivity are also known (U.S. Pat. No. 3,893,888). Such amino acid producers remain auxotrophic and can grow only on media containing specific additives.

Known in the art is also a method for preparing bacterial strains that produce amino acids which is based on the isolation of chromosome DNA fragments of a donor bacterium containing genes controlling the synthesis of a selected amino acid, combining them with a multicopy plasmid DNA molecule by in vitro manipulation, and transforming a recipient strain with a hybrid DNA molecule to yield a bacterial strain possessing increased productivity (U.S. Pat. Nos. 4,278,765; 4,391,907). According to this method chromosomal DNA fragments are isolated from a strain a having a mutation which destroys the negative regulation of selected amino acid biosynthesis. The recipient strain may be a specially constructed strain or it may be the donor strain.

However no effective *Escherichia coli* strains producing isoleucine or valine have been obtained by this method. Therefore a need continues to exist for the development of a novel method for preparing amino acid producing strains.

Hitherto unknown are strains characterized by increasing production of an amino acid due to mutation in genes coding for the corresponding aminoacyl-tRNA synthetase. The aminoacyl-tRNA synthetases, or activating enzymes, are particularly crucial elements in the route leading from amino acids to proteins. These enzymes catalyze the formation of activated amino acids, that is their attachment to one or more specific tRNA. In most cases there is but one aminoacyl-tRNA synthetase for each amino acid. So, only conditionally expressed mutations may be obtained.

Mutants with altered aminoacyl-tRNA synthetases were described in several papers:

1. Roth, J. R., and Ames, B. N., *J. Mol. Biol.*, v. 22, p. 325, 1966.

2. Neidhardt, F. C., *Bacteriol. Rev.*, v. 30, p. 701, 1966.

3. Folk, W. R., and Berg, P., *J. Bacteriol.*, v. 102, p. 193, 1970.

4. Iaccarino, M., and Berg, P., *J. Bacteriol.*, v. 105, p. 527, 1971.

5. Johnson, E. M. et al, *J. Bacteriol.*, v. 129, p. 66, 1979.

Some aminoacyl-tRNA synthetase mutations manifest themselves as auxotrophy. This is an unusual auxotrophy, because the defect is not in the formation of an amino acid, but in its utilization for protein synthesis. Also it was communicated, that phenotypic suppression of such auxotrophic mutations may arise as a result of additional mutations which increase the biosynthesis and intracellular concentration of the corresponding amino acid. However, amino acid producing strains constructed on the basis of auxotrophic aminoacyl-tRNA synthetase mutations and methods for their production were not known. Also, the role of such mutations in overproduction of amino acids by producer strains was not established.

SUMMARY OF THE INVENTION

It is an object of the present invention to use aminoacyl-tRNA synthetase mutations for preparing strains possessing enhanced capability of producing amino acids without additional growth factors, more specifically, strains of *Escherichia coli* producing isoleucine and valine.

3

These and other objects of the invention have been attained by development of a method for preparing strains which produce enhanced levels of amino acids due to a mutation affecting aminoacyl-tRNA synthetase conferring cells auxotrophy which can be compensated only partially by addition of the selected amino acid into the culture medium. This is combined with mutations which destroy the negative regulation of the amino acid biosynthesis to give a strain capable of increased productivity of the selected amino acid.

DETAILED DESCRIPTION OF THE INVENTION

Mutations affecting aminoacyl-tRNA synthetases which manifest themselves as auxotrophy have many times decreased affinity (increased the Km) for the corresponding amino acids (3-4). Therefore the formation of the activated amino acids (the charging of the corresponding tRNA) in their cells is decreased. Under this condition the transcription of the structural genes (operons) involved in the biosynthesis of these amino acid may be markedly increased, if this expression is controlled by attenuation. This regulatory mechanism exists in many amino acid operons of different bacterial species (Kolter, R., Yanofsky, C., *Ann. Rev. Genet.*, v. 16, p. 113, 1982; Matsui, K. et al, *Nucleic Acids Res.*, v. 14, p. 10113, 1986; Shimotsu, H. et al, *J. Bacteriol.*, v. 166, p. 461, 1986; Kuroda, M. I. et al, *J. Bacteriol.*, v. 167, p. 792, 1986).

Besides, the decreased tRNA charging elevates the intracellular concentration of guanosinetetraphosphate (ppGpp), which is known to activate initiation of transcription of amino acid operons (Stephens, J. C. et al, *Proc. Nat. Acad. Sci. USA*, v. 72, p. 389, 1975; Cashel, M., and Rudd, K. E., In: *"Escherichia coli* and *Salmonella typhimurium*: Cellular and Molecular Biology (vol. 12, Neidhardt, F. C., ed,), p. 1410, ASM, Washington, 1987). Taken together these factors create the possibility for overproduction of the corresponding amino acid. This possibility can be realized if the negative regulation of the amino acid biosynthesis is eliminated.

To obtain the high level of amino acid operons expression, which is necessary for effective amino acid production, only those aminoacyl-tRNA synthetase mutations must be used which cannot be fully suppressed (compensated) by addition of the corresponding amino acid into the medium. These mutations may be produced by conventional process for mutation induction such as by treating the prototrophic parent strain with N-methyl-N'-nitro-N-nitrosoguanidine. The screening procedure should include selection of auxotrophic mutants, which can grow only slowly on media containing high concentrations (3-10 mg/ml) of the corresponding amino acid, and cannot grow without it. This procedure permits one to obtain just the mutants with impaired aminoacyl-tRNA synthetases, because the auxotrophy caused by blocks in the amino acid biosynthetic pathway can be completely compensated by addition of low concentrations (0.005-0.05 mg/ml) of the amino acid into the medium.

on the basis of the mutant strains additional mutations, those with increased intracellular concentration of the corresponding amino acid may be obtained by selecting (pseudo)revertants, which can grow on media containing no amino acid or containing low concentrations of the amino acid. By using this procedure different mutations in the genes involved in amino acid overproduction may be induced, and step-by-step selection leading to increased amino acid productivity may be performed. Maintenance of the defect in the aminoacyl-tRNA synthetase in revertants must have positive effect on their productivity. Thus, effective amino acid producing strains may be prepared.

In addition, these types of mutations affecting aminoacyl-tRNA synthetase may be introduced into the chromosome of amino acid producers obtained by known procedures, including selection for analogue-resistance, by transformation, transduction, conjugation or protoplast fusion to increase their productivity. Also, the above-described mutations affecting aminoacyl-tRNA synthetases may be introduced into the chromosome of recipient strains by recombinant DNA techniques.

Using the method of the present invention, mutant strains were constructed which produce valine and isoleucine in higher yields than has been achieved with previously known methods using artificial mutants of Escherichia.

Having generally described this invention, a further understanding can be obtained by reference to certain specific examples which are given for illustration and not intended to be limiting.

EXAMPLE 1

1. Selection of mutants requiring high isoleucine concentration for their growth.

*Escherichia coli* K12 W3350 was treated with N-methyl-N'-nitro-N-nitrosoguanidine and cultured with shaking in the presence of 10 mg/ml of L-isoleucine at 37° C. for 24 hours. The cells were then washed, resuspended in minimal medium supplemented with glucose (0.2%) and washed at 37° C. When a doubling of optical density (A590) was obtained, 2000 units of penicillin per ml was added, and after 3 hours incubation at 37° C. the cells were washed and spread on minimal agar plates supplemented with 0.2% glucose and 10 mg/ml L-isoleucine. Isoleucine auxotrophs which can grow only in the presence of high isoleucine concentration in the medium were selected using the standard procedure. Three independent mutants have thus been isolated: IeS2, IleS17, and IleS32. IleS2, IleS17 and IleS32 have been deposited under the provisions of the Budapest Treaty with the Russian National Collection of Industrial Microorganisms (VKPM), VNIIGENETICA(USSR 113545 Moscow, 1 Dorozhny proezd, 1,), under accession numbers B-5509, B-5510 and B-5515, respectively, on Jul. 12, 1994.

Table 1 shows the optical densities (A590) of the 18 hour cultures of the isoleucine-requiring mutants grown on minimal medium supplemented with different isoleucine concentrations.

TABLE 1

| | isoleucine (mg/ml) | | | | | |
| --- | --- | --- | --- | --- | --- | --- |
| | 0.00 | 0.01 | 0.05 | 1.0 | 3.0 | 5.0 |
| Strain | Optical density (A590) | | | | | |
| IleS 2 | 0.001 | 0.18 | 0.33 | 1.10 | 1.30 | 1.60 |
| IleS 17 | 0.001 | 0.013 | 0.04 | 0.11 | 0.41 | 0.76 |
| IleS 32 | 0.001 | 0.14 | 0.29 | 1.00 | 2.00 | 2.00 |
| VL 330 | 0.001 | 0.93 | 1.70 | 1.60 | 1.40 | 1.40 |
| W 3350 | 1.50 | 1.70 | 2.00 | 2.00 | 2.00 | 2.00 |

The regular isoleucine auxotroph VL 330 (ilvA) reaches the maximum OD at 0.05 mg/ml of isoleucine in a growth medium. The mutants IleS2, IleS17 and IleS32 require much higher isoleucine concentration for their growth. Furthermore, the mutant IleS17 grew slowly even in the presence of 5 mg/ml of isoleucine in the medium.

Genetic data has shown that mutations conferring isoleucine auxotrophy to the IleS strains were mapping on the *Escherichia coli* chromosome between the threonine and leucine operons where the gene coding for isoleucyl-tRNA synthetase is known to be located. Accordingly, isoleucyl-tRNA synthetase activities in the IleS2 and IleS17 strains measured by a known method were 43% and 37% of the respective activity in the parental strain *Escherichia coli* W 3350.

2. Selection of the mutants requiring high valine concentration for their growth.

*Escherichia coli* VL1502 (valR, pyrB::Tn5), W 3350 derivative was treated with N-methyl-N'-nitro-N-nitrosoguanidine and cultivated with aeration in the presence of 10 mg/ml of L-valine at 37° C. for 30 hours. Then, after two rounds of the penicillin enrichment procedure described above, valine auxotrophs were selected. About 20% of colonies tested were valine-requiring. Nine independent ValS mutants have thus been isolated.

Table 2 shows the optical densities (A590) of 20 hour cultures of some ValS mutants grown on minimal medium supplemented with valine in different concentrations.

TABLE 2

| | valine (mg/ml) | | | | | | | | |
|---|---|---|---|---|---|---|---|---|---|
| | 0.00 | 0.05 | 0.2 | 0.5 | 1.0 | 2.0 | 5.0 | 7.0 | 10.0 |
| Strain | Optical density (A590) | | | | | | | | |
| ValS 52 | 0.005 | 0.01 | 0.02 | 0.03 | 0.07 | 0.16 | 1.5 | 1.8 | 1.4 |
| ValS 67 | 0.01 | 0.04 | 0.07 | 0.21 | 0.50 | 1.8 | 2.2 | 1.9 | 1.5 |
| VAlS 91 | 0.02 | 0.03 | 0.04 | 0.08 | 0.15 | 0.58 | 1.9 | 1.8 | 1.45 |
| C600 ilvC* | 0.01 | 2.0 | 2.2 | 2.3 | 2.2 | 2.9 | 2.3 | 2.2 | 2.2 |

*For this strain 0.1 mg/ml of isoleucine was added together with indicated valine concentrations All the mutations conferring valine-requirement to ValS mutants were cotransduced with high frequency by phage P1 with pyrB::Tn5 marker (82–96%). This result indicates that they are located in the same region where known ValS mutations were mapped. Activity of valyl-tRNA synthetase was measured by a known method in several ValS mutants and found to be decreased. In ValS52 mutant it was only 16% of the respective activity in the parental strain.

Thus, by using the described procedure mutants impaired in aminoacyl-tRNA synthetase activities can easily be selected.

3. Measuring of guanosinetetraphosphate level in IleS 17 mutant.

During the balanced growth IleS and ValS mutants may have decreased levels of charged isoleucyl-tRNA or valyl-tRNA due to reduced activity of the corresponding aminoacyl-tRNA synthetase. This must lead to the increased formation of guanosinetetraphosphate (ppGpp). So intracellular ppGpp concentration was measured by using a known method in the IleS17 mutant and in the parental strain W3350 grown in minimal medium supplemented with isoleucine.

TABLE 3

| Strain | Isoleucine concentration in medium (mg/ml) | ppGpp pmole/A450 |
|---|---|---|
| W3350 | 2 | 35 |
| IleS17 | 2 | 140 |
| | 3 | 105 |
| | 5 | 55 |
| | 10 | 30 |

The results presented in Table 3 show that under the same growth conditions the ppGpp concentration in IleS17 mutant is four times higher than in the strain W3350. The ppGpp level was dependent on isoleucine concentration in growth medium. The higher was the isoleucine concentration the lower was the level of ppGpp in IleS17 cells.

4. Determination of threonine deaminase activity in IleS mutants.

Isoleucine and valine production by *Escherichia coli* strains must depend on the level of ilv-operon expression. To determine the effect of ileS mutations on expression of the ilvGMEDA operon the threonine deaminase activity was measured by a known method in IleS mutants grown on medium supplemented with isoleucine in low (0.01 or 0.05 mg/ml) and high (5.2 mg/ml) concentrations (Table 4).

TABLE 4

| Strain | Isoleucine concentration in medium (mg/ml) | Relative threonine deaminase activity (%) |
|---|---|---|
| IleS 2 | 0.01 | 757 |
| | 5.20 | 87 |
| IleS 17 | 0.05 | 658 |
| | 5.20 | 366 |
| IleS 32 | 0.01 | 682 |
| | 5.20 | 122 |
| W3350 | 0.00 | 100 |
| | 5.20 | 26 |

The results presented in Table 4 show that the enzyme activities in the IleS strains were higher than in the parental strain W3350 under different growth conditions. It can also be seen that in the presence of 5.20 mg/ml of isoleucine in medium the highest threonine deaminase activity was in the IleS17 mutant (14 times higher than in W3350).

EXAMPLE 2

1. Selection of revertants of IleS strains which produce isoleucine.

The strains IleS2, IleS17 and IleS32 were treated with N-methyl-N'nitro-N-nitrosoguanidine, spread on plates containing minimal medium supplemented with 0.2% glucose or 0.2% glucose and 3 mg/ml threonine and cultured for 48–72 hours. The revertants which appeared were tested for their ability to excrete isoleucine into a medium and to feed the lawn of isoleucine-requiring mutant IlvA (syntrophism test, Table 5).

TABLE 5

| Parent strain | Number of revertants tested | Number of isoleucine excretors |
|---|---|---|
| IleS 2 | 50 | 14 |
| Iles 17 | 100 | 25 |
| IleS 32 | 75 | 24 |

Thus, using IleS mutants isoleucine producing strains can easily be obtained.

Threonine deaminase activity and its inhibition by the end product was determined in revertants excreting isoleucine. In most of them the enzyme was not inhibited by 1 mM of isoleucine. Furthermore, in the revertant Rev 7434 (derivative of IleS2) threonine deaminase was completely insensitive to inhibition by the end product. Genetic and nucleotide sequence analysis of Rev 7434 has shown that the mutation conferring resistance to the inhibition was in the ilvA gene coding for threonine deaminase (ilvA7434 mutation).

2. Construction of the isoleucine producing strain containing valR, ilvA7434, and ileS17 mutations.

The strain Rev7434, as well as other *Escherichia coli* K12 strains, contains a mutation in the ilvG gene which decreases the ilvGMEDA operon expression. To eliminate this defect a spontaneous valine-resistant mutant of this strain was obtained by plating it on agar minimal medium supplemented with glucose (0.2%) and L-valine (1 mg/ml). Thus, ValR strain VL1886 was obtained which contains a mutation conferring valine-resistance located in the ilvGMEDA operon. Phage P1 grown on the strain VL1886 was used for transduction of the strain VL334 (thrC ilvA). On minimal medium supplemented with glucose (0.2%) and threonine (0.05 mg/ml) Ile+ transductants were selected. Over 90% of them were valine-resistant and had threonine deaminase insensitive to inhibition by isoleucine. Thus the strain VL1887 (thrC ilvA7434 valR) was obtained. Then phage P1 grown on IleS17 was used for transduction of the strain VL1887. On minimal medium supplemented with glucose Thr+ transductants were selected. About 50% of them grew slowly, and their growth was stimulated by isoleucine. These were transductants which received ileS17 mutation. Thus the strain VL1892 was constructed which contains simultaneously, valR, ilvA7434, and ileS17 mutations. This strain had elevated levels of isoleucine-insensitive threonine deaminase which was from 6 to 10 times higher than in Rev7434. The syntrophism test showed that the strain VL 1892 produces isoleucine.

3. Construction of the isoleucine producing strain containing ilv-operons on low copy number plasmid.

The strain AB 1206 harbors a low copy number plasmid F'14, which contains a chromosome fragment with ilv-operons and a corresponding chromosome deletion. Phage P1 grown on VL1886 was used for transduction of AB 1206. The transductants were selected on minimal medium supplemented with-glucose (0.2%) and valine (1 mg/ml). Thus the stain KX 139 was obtained in which the F'14 plasmid contains the valR and ilv7434 mutations established by measuring threonine deaminase activity by a known method. The plasmid can be transferred by conjugation in different *Escherichia coli* strains, more specially, in IleS17. However in RecA+ strains it might be unstable because of the frequent integration into the chromosome. Therefore the recA mutation was introduced into the chromosome of IleS17 strain by using the known conjugation procedure from the strain NK6659 (Hfr KL16 srl::Tn10 recA). Recombinants were obtained on. L-broth agar medium supplemented with tetracycline (0.01 mg/ml) and among them a UV-sensitive IleS strain was selected. Thus the strain KX140 having genotype ileS17 recA was prepared. The plasmid F'14 (valR ilv7434) was introduced into the cells of KX140 by conjugation giving the strain KX 141. The syntrophism test showed that this strain produces isolrus.

4. Production of L-isoleucine by the novel L-isoleucine-producing strains.

The strains of *Escherichia coli* VL 1892 and KX141 were inoculated by loop from the slant of an agarized M9 medium into Erlenmeyer flasks each containing 50 ml of L-broth (containing 10 g/l peptone, 5 g/l yeast extract, 1 g/l glucose and 5 g/l NaCl, pH 7.2). After inoculation the flasks were placed on a circular shaker (200 r.p.m.) and incubated for 18 hours at the temperature 37° C. The thus prepared material was used as a seed culture.

A main culture medium, containing 30 g/l glucose, 5 g/l ammonium sulfate, 2 g/l $K_2HPO_4$, 0.4 g/l $MgSO_4.7H_2O$, 0.02 g/l $FeSO_4.7H_2O$, 0.02 g/l $MnSO_4.5H_2O$, 2 g/l yeast autolysate, 1 g/l L-threonine was prepared. 300 ml of the medium was placed in a 0.5 l jar-fermentor and sterilized at 121° C. for 15 min. The medium was inoculated with 30 ml of the seed culture obtained above and cultivated with stirring at 900 r.p.m. and introducing 1:1 volume of air per minute. The pH of the medium was maintained automatically around 7.2 by feeding, on pH-monitor signal, a mixture containing in ratio 10:7:1 of 10% solution of threonine, 60% solution of glucose, and 25% solution of ammonia.

The fermentation was performed for 46 hours. By the end of fermentation the culture medium with VL1892 contained 8–13 g/l of isoleucine, and the culture medium with KX 141 contained 11–17.8 g/l of isoleucine. The strains KX141 and VL1892 have been deposited in the All-Union Collection of Industrial Microorganisms in VNIIGENETIKA(USSR) under accession numbers B-4781 and B-4410, on Sep. 12, 1991 and Jul. 12, 1994, respectively.

EXAMPLE 3

1. Selection of the revertants of IleS32 ValR strain which produce L-valine.

To obtain L-valine producers, the strain harboring both ileS and valR (ilvG) mutations was constructed. The valR (ilvG) mutation restores the activity of the valine-resistant AHAS II—the key enzyme in valine biosynthetic pathway, which is defective in the strains of *E. coli* K12. By sequential phage P1-mediated transduction mutation valR from the strain C600 valR (resistant to 1 mg/ml of valine) and mutation ileS32 from the strain IleS32 were introduced into the chromosome of the strain VL334 (thrC ilvA). On the plates of agarized minimal medium M9, containing glucose (0.2%) and valine (2 mg/ml), ValR transductants were selected and on the plates of this medium containing isoleucine (2 mg/ml) Thr+ IleS transductants were obtained.

Thus the strain IleS32 valR was constructed. Then the revertants of this strain were selected by plating it on M9 medium containing no isoleucine. The colonies which appeared were tested for their ability to feed the lawn of isoleucine and valine requiring *E. coli* strain on minimal medium M9 containing isoleucine (0.05 mg/ml). Thus valine excreting strains Rev835, Rev 839 and Rev874 were obtained.

By using phage P1-mediated transduction it was found that all of the revertants contained ileS mutation which can be transferred in different *Escherichia coli* strains.

2. Production of L-valine by the (pseudo)revertants.

The ability of the strains obtained to produce L-valine was tested by fermentation in tubes. The fermentation medium contained 50 g/l glucose, 10 g/l ammonium sulfate, 1 g/l $K_2HPO_4$, 0.4 g/l $MgSO_4.4H_2O$, 0.02 g/l $FeSO_4.7H_2O$, 0.02 g/l $MnSO_4.5H_2O$, and 20 g/l $CaCO_3$ (separately sterilized) and the pH was adjusted to 7.2.

Three ml batches of the fermentation medium were placed in 20 mm tubes inoculated with one loopful inoculum of the test strain cells, and cultivation was carried out at 37° for 46 hours.

The amount of L-valine in the supernatants of the fermentation broth is shown in Table 6.

TABLE 6

| Strain tested | L-valine produced (g/l) |
| --- | --- |
| Rev 835 | 4.3 |
| Rev 839 | 1.2 |
| Rev 874 | 5.6 |

3. Construction of the effective L-valine producer.

To obtain a more effective valine producer and to find out the role of ileS mutations on valine production, isogenic IleS+ and IleS− were constructed on the basis of Rev 874. Phage P1, cultured on the cells of donor strain NK 6066 (thr::Tn9) was used for transduction of thr:Tn9 into the chromosome of the Rev 874. The transductants were selected on L-broth agar plates, containing chloramphenicol (10 ug/ml). Among them threonine-requiring strain VL 1966, fast-growing on minimal medium containing no isoleucine (IleS+), was obtained. The cells of this strain were transduced by phage P1 grown on IleS17. The transductants were selected on M9 minimal medium containing glucose (0.2%) and isoleucine (2 mg/ml). Among Thr+ recombinants two strains, VL1968 (IleS+) and VL1970 (IleS17) were obtained. We tested the productivity of these strains as well as of the strain Rev874, culturing them as described above. The productivity was calculated as a ratio of valine concentration in the culture medium to the optical density of the cultures. The results are presented in Table 7.

TABLE 7

| Strain tested | IlsS allel | Valine productivity g/l/OD560 |
|---|---|---|
| VL1968 | ileS+ | 0.01 |
| VL1970 | ileS17 | 0.76 |
| Rev 874 | ileS32 | 0.52 |

It can be seen from Table 7 that ileS mutations markedly enhance valine productivity of *E. coli* valine producers. Besides, mutation ileS17 which is only partially suppressed by addition of isoleucine into the medium has a more pronounced effect on valine productivity. The more effective valine producer strain VL 1970 was constructed by combining in one bacterial genom mutation(s) in ilv operon, which have positive effects on valine production, with mutation ileS17, which impairs isoleucyl-tRNA synthetase and can be suppressed only partially by addition of exogenous isoleucine into a medium.

4. Production of L-valine by the novel *Escherichia coli* strain VL1970.

*E. coli* VL1970 was cultivated at 37° C. for 18 hours in Erlenmeyer flasks with agitation (300 rpm) on the seed culture medium. It was minimal medium M9 with glucose (1%). A main culture medium, containing 30 g/l glucose, 5 g/l ammonium sulfate, 2 g/l $K_2HPO_4$, 0.4 g/l $MgSO_4.7H_2O$, O, 0.02 g/l $FeSO_4.7H_2O$, 0.02 g/l $MnSO_4.5H$ O, 0.6 g/l NaCl and 0.25 g/l yeast autolysate, pH 7.2, was prepared.

300 ml of the medium was placed in a 0.5 liter jar-fermentor and sterilized at 121° C. for 15 minutes. The medium was inoculated with 30 ml of the seed culture obtained above, and cultivated at 37° C. with stirring at 900 rotations per minute and introducing 1:1 volume of air per minute. The pH of the medium was maintained automatically around 7.2 by introducing in the fermentor, on pH-monitor signal, the mixture containing a ratio of 6:1 50% glucose and 25% ammonia. The fermentation was performed for 46 hours. By the end of the fermentation the culture medium contained from 8.2 to 10.6 g/l of valine. This was 7 times more than obtained by using an *E. coli* strain constructed by recombinant DNA techniques.

The strain VL1970 has been deposited in the All-Union Collection of Industrial Microorganisms in VNIIGENETIKA(USSR) as VKPM B-4411.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of producing L-isoleucine comprising:
   (i) culturing a revertant *Escherichia coli* strain in a nutrient medium, (ii) accumulating L-isoleucine in the medium, and (iii) collecting L-isoleucine from the medium, wherein said revertant *Escherichia coli* strain is prepared by (a) contacting a strain of *Escherichia coli* selected from the group consisting of IleS2, IleS17, and IleS32 with a mutating agent to obtain mutants, (b) screening said mutants for the ability to excrete isoleucine and (c) selecting a mutant which excretes isoleucine, to obtain said revertant *Escherichia coli* strain.

2. The method of claim 1, wherein said mutating agent is N-methyl-N'-nitro-N-nitrosoguanidine.

3. A method of producing L-isoleucine comprising:
   (i) culturing a L-isoleucine-producing strain of *Escherichia coli* in a nutrient medium, (ii) accumulating L-isoleucine in the medium, and (iii) collecting L-isoleucine from the medium, wherein said L-isoleucine-producing strain of *Escherichia coli* is prepared by (a) contacting a strain of *Escherichia coli* selected from the group consisting of IleS2, IleS17, and IleS32 with a mutating agent to obtain mutants, (b) screening said mutants for the ability to excrete isoleucine, (c) selecting a mutant which excretes isoleucine to obtain a revertant strain of *Escherichia coli*, (d) plating said revertant strain on medium containing L-valine to obtain a valine-resistant mutant of *Escherichia coli*, (e) transducing a strain of *Escherichia coli* which has a threonine deaminase operon which is insensitive to inhibition by isoleucine with phage P1 grown on said valine-resistant mutant of *Escherichia coli* to obtain a transductant which is valine-resistant and has a threonine deaminase operon which is insensitive to inhibition by isoleucine, and (f) transducing said transductant with phage P1 grown on a strain of *Escherichia coli* selected from the group consisting of IleS2, IleS17, and IleS32, to obtain said L-isoleucine-producing strain of *Escherichia coli*.

4. The method of claim 3, wherein said mutating agent is N-methyl-N'-nitro-N-nitrosoguanidine.

5. The method of claim 3, wherein said strain of *Escherichia coli* is VL 1892.

6. A method of producing L-isoleucine comprising:
   (i) culturing a L-isoleucine-producing strain of *Escherichia coli* in a nutrient medium, (ii) accumulating L-isoleucine in the medium, and (iii) collecting L-isoleucine from the medium, wherein said L-isoleucine-producing strain of *Escherichia coli* is produced by transforming a strain of *Escherichia coli* selected from the group consisting of IleS2, IleS17 and IleS32 and strains transduced with phage P1 grown thereon with a recombinant DNA which contains (a) a gene encoding valine resistance and (b) a threonine deaminase operon which is insensitive to inhibition by isoleucine, to obtain said L-isoleucine-producing strain of *Escherichia coli*.

7. The method of claim 6, wherein said strains transduced with phage P1 harbor plasmid F'14.

8. The method of claim 6, wherein said L-isoleucine-producing strain of *Escherichia coli* is KX 141.

9. The method of claim 6, wherein said strain of *Escherichia coli* selected from the group consisting of IleS2, IleS17 and IleS32 is conjugated with the strain NK 6659 to obtain a strain having the recA mutation prior to said transfecting.

* * * * *